United States Patent
Jain et al.

(10) Patent No.: US 10,198,815 B2
(45) Date of Patent: Feb. 5, 2019

(54) METHOD AND SYSTEM FOR ANALYZING IMAGE DATA

(71) Applicant: ICOMETRIX NV, Leuven/Winksele (BE)

(72) Inventors: Saurabh Jain, Heverlee (BE); Dirk Smeets, Bierbeek (BE); Diana Sima, Haacht (BE); Annemie Ribbens, Heverlee (BE); Anke Maertens, Wilsele (BE)

(73) Assignee: ICOMETRIX NV, Leuven/Winksele (BE)

( * ) Notice: Subject to any disclaimer, the term of this patent is extended or adjusted under 35 U.S.C. 154(b) by 0 days.

(21) Appl. No.: 15/510,151

(22) PCT Filed: Sep. 9, 2015

(86) PCT No.: PCT/EP2015/070663
§ 371 (c)(1),
(2) Date: Mar. 9, 2017

(87) PCT Pub. No.: WO2016/038118
PCT Pub. Date: Mar. 17, 2016

(65) Prior Publication Data
US 2017/0256056 A1    Sep. 7, 2017

(30) Foreign Application Priority Data

Sep. 9, 2014  (EP) .................................. 14184117

(51) Int. Cl.
*G06K 9/00* (2006.01)
*G06T 7/00* (2017.01)
(Continued)

(52) U.S. Cl.
CPC .......... *G06T 7/0014* (2013.01); *G06K 9/4604* (2013.01); *G06K 9/628* (2013.01);
(Continued)

(58) Field of Classification Search
None
See application file for complete search history.

(56) References Cited

U.S. PATENT DOCUMENTS

| 5,983,251 A * | 11/1999 | Martens | H04N 19/186 |
| | | | 375/E7.083 |
| 2016/0034638 A1* | 2/2016 | Spence | C12Q 1/6869 |
| | | | 702/19 |

OTHER PUBLICATIONS

Boer et al., "White Matter Lesion Extension to Automatic Brain Tissue Segmentation on MRI," Neuroimage, vol. 45, 2009, pp. 1151-1161.

(Continued)

*Primary Examiner* — Atiba O Fitzpatrick
(74) *Attorney, Agent, or Firm* — Workman Nydegger (57) ABSTRACT

A method of analyzing image data comprises: obtaining a first image of a first part of an object; obtaining a second image of a second part of the object having overlap with the first part; obtaining a mapping between the first and second images; segmenting the second image to obtain a segmentation; detecting outliers in the first image by identifying extreme intensity values of elements within one or more classes of elements on the basis of the segmentation; replacing elements of the second image that correspond to at least some outliers of the first image, with replacement values, to obtain a corrected second image; and updating the segmentation by performing the segmenting on the corrected second image. The detecting outliers, the replacing, and the updating are performed iteratively until a predetermined convergence criterion is met, which represents a point where there is no significant change in the tissue and lesion segmentations.

12 Claims, 4 Drawing Sheets

(51) Int. Cl.
G06T 7/11 (2017.01)
G06T 7/143 (2017.01)
G06T 7/174 (2017.01)
G06T 7/62 (2017.01)
G06K 9/46 (2006.01)
G06K 9/62 (2006.01)
G06T 3/00 (2006.01)
G06T 11/00 (2006.01)

(52) U.S. Cl.
CPC .............. *G06T 3/0068* (2013.01); *G06T 7/11* (2017.01); *G06T 7/143* (2017.01); *G06T 7/174* (2017.01); *G06T 7/62* (2017.01); *G06T 11/008* (2013.01); *A61B 2576/026* (2013.01); *G06T 2207/10084* (2013.01); *G06T 2207/10088* (2013.01); *G06T 2207/20128* (2013.01); *G06T 2207/30016* (2013.01); *G06T 2207/30096* (2013.01)

(56) References Cited

OTHER PUBLICATIONS

Spies et al., "Fully Automatic Detection of Deep White Matter T1 Hypointense Lesions in Multiple Sclerosis," Physics in Medicine and Biology, vol. 58, 2013, pp. 8323-8337.

Hadjidemetriou et al., "Computational Atlases of Severity of White Matter Lesions in Elderly Subjects with MRI," Miccai, Part 1, LNCS 5241, pp. 450-458, 2008.

Ong et al., "Automated White Matter Lesion Segmentation in MRI Using Box-Whisker Plot Outlier Detection," Retrieved from the Internet URL:http://www2.warwick.ac.uk/fac/sci/dcs/events/past/miua2010/proceedings/paper_60, 2010, 5 pages.

Schmidt et al., "LST: A Lesion Segmentation Tool for SPM Manual for Version 1.2.3," Retrieved from the Internet, http://www.applied-statistics.de/LST_manual.pdf, Mar. 12, 2013, 12 Pages.

Schmidt et al., "An Automated Tool for Detection of FLAIR-Hyperintense White-Matter Lesions in Multiple Sclerosis," Neuroimage, vol. 59, 2012, pp. 3774-3783.

Valverde et al., "NeuroImage: Clinical," Neuroimage: Clinical 6, 2014, pp. 86-92.

Battaglini et al., "Evaluating and Reducing the Impact of White Matter Lesions on Brain Volume Measurements," Human Brain Mapping, vol. 33, 2012, pp. 2062-2071.

Cardoso et al., "Adaptive Neonate Brain Segmentation," MICCAI, Part III, LNCS 6893, 2011, pp. 378-386.

Modat et al., "Efficient Dense Non-Rigid Registration Using the Free-Form Deformation Framework," Centre for Medical Image Computing University College London, Jan. 22, 2012, 131 Pages.

Modat et al., "Fast Free-Form Deformation Using Graphics Processing Units," Computer Methods and Programs in Biomedicine, vol. 98, 2010, pp. 278-284.

Ourselin et al., "Robust Registration of Multi-Modal Images: Towards Real-Time Clinical Applications," MICCAI, LNCS 2489, 2002, pp. 140-147.

Souplet et al., "An Automatic Segmentation of T2-FLAIR Multiple Sclerosis Lesions," MICCAI 2008 Workshop, Jul. 15, 2008, 12 Pages.

Leemput et al., "Automated Segmentation of Multiple Sclerosis Lesions by Model Outlier Detection," IEEE Transactions on Medical Imaging, vol. 20, No. 8, Aug. 2001, pp. 677-688.

International Search Report from PCT Application No. PCT/EP2015/070663, dated Dec. 23, 2015.

European Search Report from EP Application No. 14184117.1, dated Feb. 19, 2015.

International Preliminary Report on Patentability from PCT Application No. PCT/EP2015/070663, dated Mar. 14, 2017.

* cited by examiner

METHOD AND SYSTEM FOR ANALYZING IMAGE DATA

FIELD OF THE INVENTION

The present invention pertains to the field of digital image analysis, in particular to the analysis of medical images.

BACKGROUND

In many medical disciplines, diagnosis and follow-up of diseases relies to an ever increasing degree on the interpretation of data obtained by medical imaging techniques. In the field of neurology, magnetic resonance (MR) imaging has become particularly important, as it has specific advantages over X-ray based computerized tomography (CT) in certain situations.

In particular, the (estimated) volume of white matter lesions is used as a biomarker for some neurological diseases, in particular multiple sclerosis (MS). In past years, it has been attempted to automate the detection of such lesions on the basis of MR images.

In the article *Automated Segmentation of Multiple Sclerosis Lesions by Model Outlier Detection* (IEEE TRANSACTIONS ON MEDICAL IMAGING, VOL. 20, NO. 8, Aug. 2001), K. VAN LEEMPUT et al. present an algorithm for segmentation of multiple sclerosis lesions from multispectral magnetic resonance images. In the method described in that article, MS lesions are detected as outliers with respect to a statistical model for normal brain tissue intensities in MR images.

In the article *An Automatic Segmentation of T2-FLAIR Multiple Sclerosis Lesions* (The MIDAS Journal—MS Lesion Segmentation (MICCAI 2008 Workshop)), JC. SOUPLET et al. present a method designed to detect a hyperintense signal area on a T2-FLAIR sequence. The disclosed algorithm uses three conventional MRI sequences: T1, T2 and T2-FLAIR. First, images are cropped, spatially unbiased and skull-stripped. A segmentation of the brain into its different compartments is performed on the T1 and the T2 sequences. From these segmentations, a threshold for the T2-FLAIR sequence is automatically computed. Then postprocessing operations select the most plausible lesions in the obtained hyperintense signals.

In the article *Evaluating and Reducing the Impact of White Matter Lesions on Brain Volume Measurements* (Human Brain Mapping Volume 33, Issue 9, 2011), M. BATTAGLINI et al. describe how the presence of white matter lesions affects certain segmentation-based brain volume measurements. The article indicates that refilling the lesions with intensities matching the surrounding normal-appearing white matter ensured accurate tissue-class measurements and thus represents a promising approach for accurate tissue classification and brain volume measurements.

There is a need for an automated way to more accurately and reliably estimate the respective volumes of white matter, gray matter, and/or cerebrospinal fluid (CSF), in the presence of lesions, in particular white matter lesions.

SUMMARY OF THE INVENTION

According to an aspect of the present invention, there is provided a method of analyzing image data, the method comprising: obtaining a first image of a first part of an object; obtaining a second image of a second part of the object, the second part having substantial overlap with the first part; obtaining a mapping between the first image and the second image; segmenting the second image to obtain a segmentation; detecting outliers in the first image by identifying extreme intensity values of elements within one or more classes of elements on the basis of the segmentation; replacing elements of the second image that correspond, according to the mapping, to at least some of the detected outliers of the first image, with replacement values, so as to obtain a corrected second image; and updating the segmentation by performing the segmenting on the corrected second image; wherein the detection outliers, the replacing, and the updating are performed iteratively until a predetermined convergence criterion is met, the predetermined convergence criterion representing a point at which there is no significant change in the tissue and the lesion segmentation.

It is an advantage of the method according to the present invention that it judiciously combines information from different types of images to extract additional information that would be extremely difficult to discern for a human observer. The invention is based inter alia on the insight of the inventors that different types of images may be more suitable for segmentation and outlier detection, respectively. The invention is further based on an insight of the inventors that different respective types of information obtained from both types of images may advantageously be combined if a mapping between two images is available, thus resulting in better segmentation and better outlier detection. The invention is further based on an insight of the inventors that this combining of information may be performed iteratively to obtain any desired balance between time consumption and accuracy of the results.

The first image and the second image may be two-dimensional or three-dimensional images, whereby the elements of the images are pixels or voxels, respectively. The object of the images may comprise biological tissues or organs, in particular tissues of the central nervous system, more in particular brain tissue. The images may have been acquired by a medical imaging technique such as magnetic resonance imaging.

In an embodiment of the method according to the present invention, the outliers are detected by segmenting the first image starting from the segmentation of the second image with an additional outlier class.

It is an advantage of this embodiment that the outliers are efficiently detected by the same general process that provides segmentation.

In an embodiment, the method according to the present invention further comprises initiating the segmenting by transferring a segmentation of an example to the second image.

It is an advantage of this embodiment that the segmenting step can be carried out in a shorter time by using an exemplary segmentation, e.g. an atlas.

In a particular embodiment, the obtaining of the mapping comprises performing a registration of the obtained first image to the obtained second image.

In cases where the mapping is not available in advance, it may be obtained as part of a method according to the present invention by means of a registration step.

In an embodiment of the method according to the present invention, the object comprises at least a part of a brain, the first image is a FLAIR image, the second image is a T1 image; the segmentation comprises a classification of elements of the T1 image as gray matter, white matter, or cerebro-spinal fluid; and the outliers are detected among elements of the first image that are classified as white matter.

This embodiment applies the principles of the invention to neurological MRI images, in order to obtain diagnostically or therapeutically relevant segmentation results.

It is a further advantage of this embodiment that the time required for image analysis with the automated method according to the present invention is much shorter than the time that would be required for manual analysis by human experts. Hence, the method of the present invention is particularly suited for processing the large numbers of images involved in clinical trials.

In a particular embodiment, the replacement values are based on average values of elements classified as white matter in non-outlier elements in proximity of said respective outliers.

The replacement values may be the actual average values of elements classified as white matter in non-outlier elements in proximity of said respective outliers, or values derived from these averages, for example by the addition of a noise term. The inventors have found that using average values, preferably with added noise, as replacement values produces very good results.

In an embodiment, the method according to the present invention further comprises removing elements representing non-brain tissue from the second image.

It is an advantage of this embodiment that the further stages of the image processing proceed in a more efficient way if the images don't contain any elements that are not relevant to the desired end result.

In an embodiment of the method according to the present invention, the segmentation is used to calculate respective volumes or areas of gray matter, white matter, and cerebrospinal fluid.

These volume or area calculations are useful to detect anomalies or changes in the distribution of these types of matter in the brain.

In an embodiment of the method according to the present invention, the outlier detection is used to calculate volumes or areas of the outliers.

This volume or area calculation is useful to detect suspected anomalies such as lesions.

In an embodiment, the method according to the present invention further comprises the calculation of volumes or areas in different anatomical regions.

It is an advantage of this embodiment that medically relevant volume or area estimates can be obtained for different anatomical regions, anomalies of which may correspond to different medical conditions. The different anatomical regions may be defined according to divisions that are in general use in the field of neurology, such as for example the division of the brain into left and right hemispheres, and into a frontal lobe, a parietal lobe, a temporal lobe, and an occipital lobe. The different anatomical regions may be defined according to a division that it is preferentially used in the diagnosis and follow-up of a specific disorder, such as multiple sclerosis, for which an exemplary division may consist of a juxtacortical region, a periventricular region, and a posterior fossa. The skilled person will appreciate that other divisions into anatomical regions may be used according to the desired type of information.

According to an aspect of the present invention, there is provided a computer program product comprising code means configured to cause a processor to carry out the method described above.

According to an aspect of the present invention, there is provided an image processing system comprising: an input interface adapted to receive a first image of a first part of an object and a second image of a second part of the object, the second part having substantial overlap with the first part; a processor, operatively connected to the input interface; and an output interface, operatively connected to the processor and adapted to output results produced by the processor; and a memory, operatively connected to the processor and arranged to comprise code to be executed by the processor, the memory comprising code configured to cause the processor to carry out the method of any of the preceding claims using the first image and the second image as inputs.

The technical effects and advantages of embodiments of the computer program product and the system according to the present invention correspond mutatis mutandis to those of the corresponding embodiments of the method according to the present invention.

BRIEF DESCRIPTION OF THE FIGURES

These and other technical aspects and advantages of embodiments of the present invention will now be described in more detail with reference to the accompanying drawings, in which.

DETAILED DESCRIPTION OF EMBODIMENTS

Figure 1:
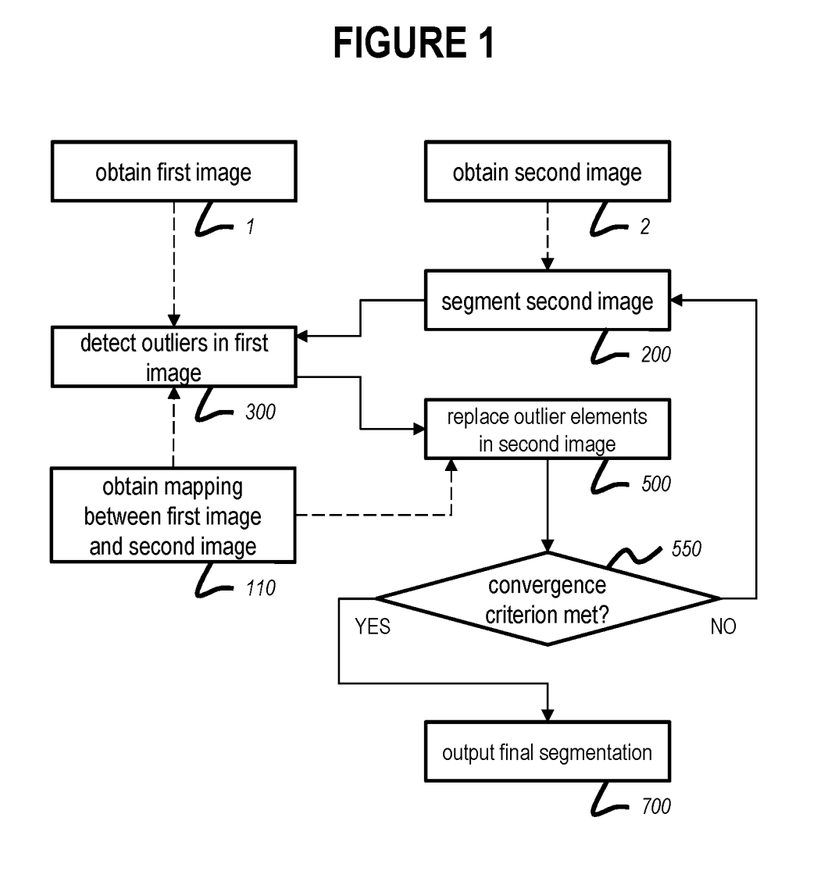
FIG. 1 provides a flow chart of a method according to an embodiment of the present invention.

FIG. 1 provides a flow chart of a method of analyzing image data according to a general embodiment of the present invention.

The illustrated method comprises obtaining 1 a first image 10 of a first part of an object and obtaining 2 a second image 20 of a second part of the object, the second part having substantial overlap with the first part. The images may be obtained from storage, or directly from an imaging device. The method further comprises obtaining a mapping 110 between the first image 10 and the second image 20. The mapping may be available from storage, or may be produced on the fly by applying a registration algorithm.

The second image 20 is segmented 200 to obtain a segmentation, i.e. different elements (pixels or voxels) of the second image 20 are classified into various predefined categories. The segmentation information is transferred to the first image 10 on the basis of the aforementioned mapping. In the first image 10, outliers are detected 300 on the basis of the segmentation; this step thus consists of identifying extreme intensity values of elements within one or more classes of elements. In the second image 20, elements that correspond, according to the mapping, to at least some of the detected outliers of the first image 10, are replaced 500 with replacement values, so as to obtain a corrected second image. The replacement values are preferably average values of elements classified within the same class in non-outlier elements in proximity of the respective outliers. The segmentation is updated by performing the segmenting 200 on the corrected second image. The detecting 300, replacing 500 and the updating 200 are performed iteratively until a predetermined convergence criterion 550 is met. The convergence criterion is advantageously defined so as to stop the iteration at a point at which there no longer is a significant change in the tissue and the lesion segmentation relative to the previous iteration. Once this criterion is met, the final segmentation information is sent to a desired output.

The present application more particularly discloses a method that measures the volumes of white matter, grey matter and cerebrospinal fluid in presence of white matter lesions based on two brain MR scans (a T1 weighted MR image and a FLAIR MR image). Moreover, the volumes of the present lesions and the parenchymal brain tissue are measured.

The lesions may be due to a brain disease such as, for example, Multiple Sclerosis (MS). The volumes of white and grey matter are important biomarkers for neurodegenerative diseases, the lesion volume for neurological diseases involving focal lesions.

Figure 2:
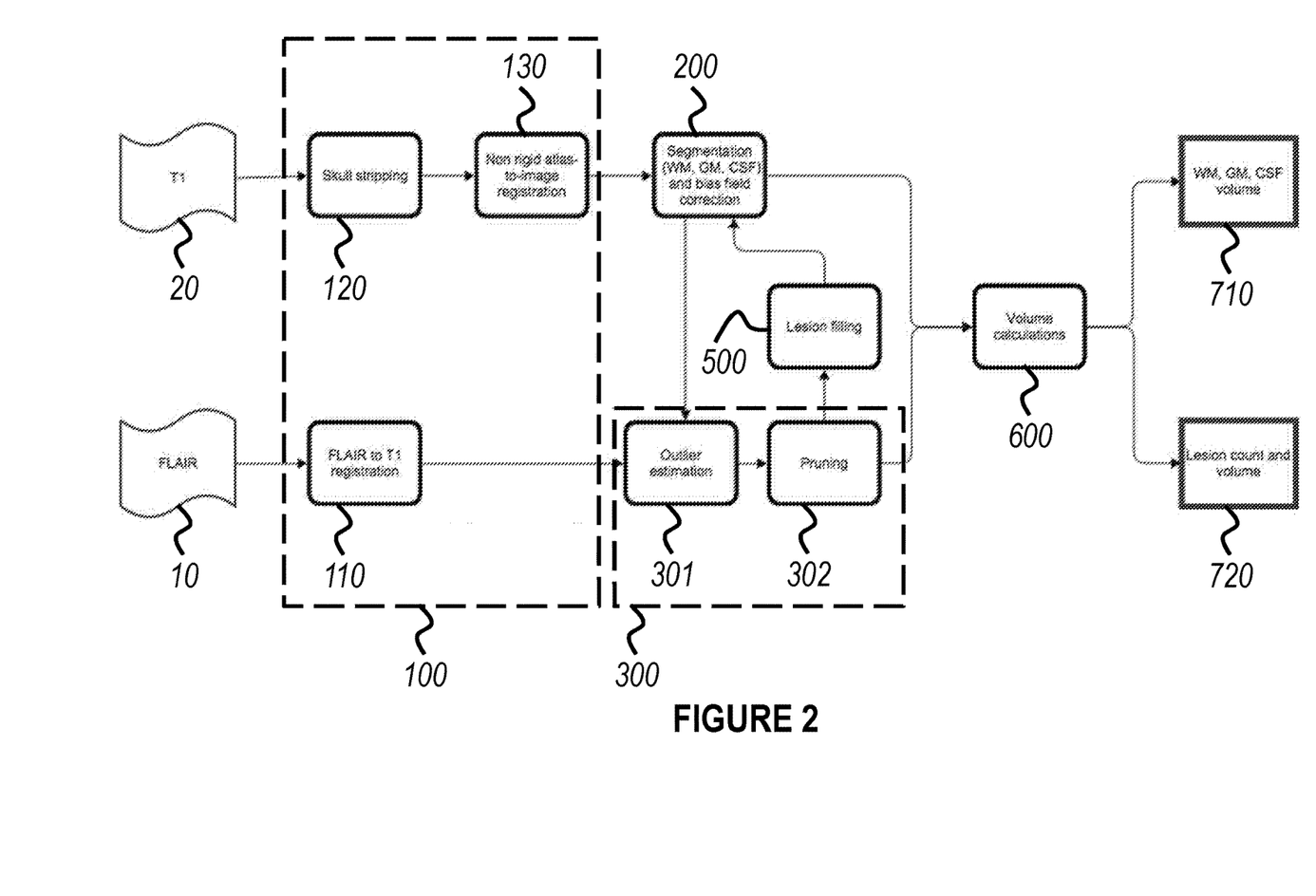
FIG. 2 provides a flow chart of a method according to another embodiment of the present invention.
Figure 3:
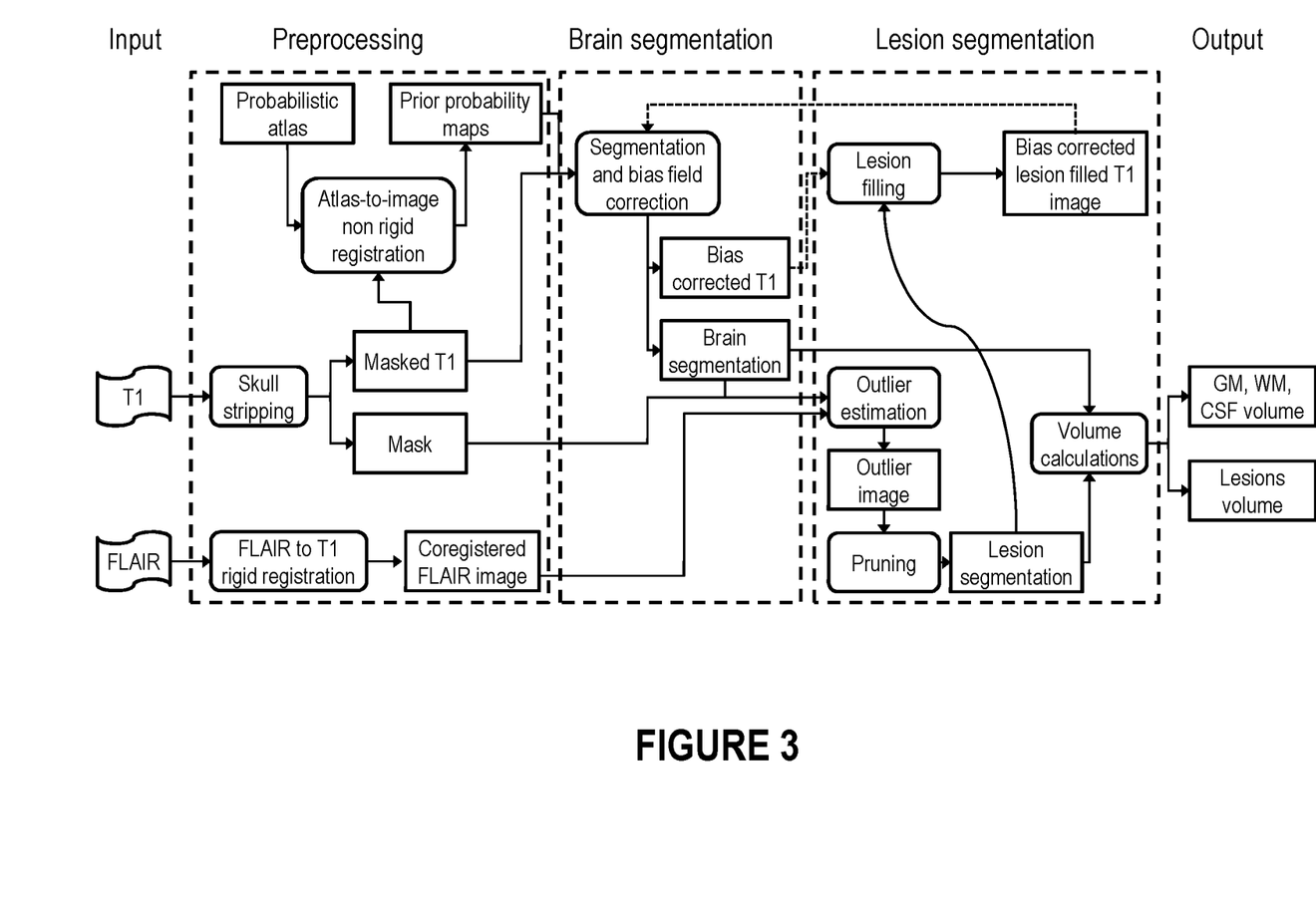
FIG. 3 provides a more detailed flow chart of the method represented in FIGS. 2.

A more particular embodiment of the method according to the present invention will now be described with reference to FIG. 2 (general overview) and FIG. 3 (detailed flow diagram). The interdependence of the various steps of the method is indicated by the arrows in the diagrams. The order in which the various steps of the method are described below is not intended to limit the invention, unless a particular temporal dependence is implicitly or explicitly given by the causal relationship between the steps.

Certain steps will be described hereinafter from a functional point of view. The skilled person will be able to carry out these steps by turning to the relevant published literature, without having to resort to undue experimentation. The relevant literature includes in particular the following publications:

S. OURSELIN et al., Robust Registration of Multi-modal Images: Towards Real-Time Clinical Applications, Medical Image Computing and Computer-Assisted Intervention (MICCAI'02);

M. MODAT et al., Fast free-form deformation using graphics processing units, Computer Methods and Programs in Biomedicine, Volume 98, Issue 3, Pages 278-284, June 2010;

M. MODAT, Efficient dense non-rigid registration using the free-form deformation framework, Doctoral Thesis University College London, 2012;

M. CARDOSO et al., Adaptive neonate segmentation, 2011 Medical Image Computing and Computer-Assisted Intervention (MICCAI'11).

The skilled person will appreciate that the following description is non-limiting and that strict adherence to the techniques described in the cited literature is not essential. Elements of the claimed invention may be implemented in a different manner without departing from the scope of the invention.

The first step 100 will be referred to as "preprocessing", and consists of three stages:

In the first stage 110, the input FLAIR image 10 of the patient is rigidly co-registered with the input T1-weighted image 20 (Ourselin et al., 2002). In the second stage 120, the T1-weighted input image 20 is skull stripped classifying each voxel either as a brain region or a non-brain region based on the affine registration of a brain mask available from an atlas (MNI) using NiftyReg (Modat et al., 2010). The registration is performed using a multi resolution affine transformation, based on the Trimmed Least Square scheme and a block-matching approach (Ourselin et al., 2002), followed by a multi resolution non-rigid registration based on the Free-Form deformation (Modat et al., 2012). In the third stage 130, the probabilistic anatomical priors for gray matter (GM), white matter (WM) and cerebrospinal fluid (CSF), which are also available from the MNI brain atlas, are transferred to the T1-weighted image space using an affine registration (Ourselin et al., 2002) followed by a non-rigid registration (Modat et al., 2010).

In the second step 200, the three probabilistic tissue priors mentioned above, together with the skull stripped T1 image 20, act as a prior knowledge to an expectation maximization (EM) algorithm (Cardoso et al., 2011). The algorithm models the intensities of each tissue class as a normal distribution, it assumes a Gaussian distributed bias field for the correction of intensity non-uniformities and it contains a spatial consistency model based on Markov Random Field (MRF). The algorithm iteratively estimates the parameters of each tissue class, as well as the bias field parameters, and maintains the spatial consistency until convergence. After the convergence of the EM algorithm, the T1 image 20 is bias corrected and segmented into the three tissue classes, i.e., GM, WM and CSF.

In the third step 301 (corresponding to a first part of step 300 of FIG. 1), the three tissue class segmentations from the previous step 200, together with the co-registered FLAIR image 10 of the same patient, are used to estimate the outliers in the FLAIR image 10. This is performed using the same expectation maximization (EM) algorithm (Cardoso et al., 2011), as described in the second step 200, but now an outlier map is included and the segmentations of the T1 image 20 are used as prior information. In other words, while modelling the intensities of each tissue class as a normal distribution, the deviation of each intensity from these normal distributions is also estimated and modelled as an outlier belief map. The algorithm iteratively estimates the outlier belief map and, after convergence, an outlier belief image is produced. This outlier belief image is an initialization for the MS lesions segmentation.

In the fourth step 302 (corresponding to a second part of step 300 of FIG. 1), the lesions are estimated from the outlier map as not every outlier is a lesion (e.g. the outlier map might include partial volume effects, artifacts, etc.). In order to differentiate the lesions from such non-lesion outliers, some extra a priori information about the location and the appearance of the lesions needs to be incorporated. In particular, the outlier map is masked. The mask is a subset of the brain mask where only intensities that are hyper intense towards GM are included. Furthermore, the outliers need to be within WM (a mask is used to exclude GM and CSF outliers as well as regions that commonly show artifacts). Finally, each outlier needs to have a minimum number of voxels.

In a fifth step 500, this lesion segmentation is then used to fill in the lesions in the bias corrected T1 image 20 with their neighborhood WM intensities.

Subsequently steps 2 (200), 3 (301), 4 (302), and 5 (500) are repeated until there is no significant change in the tissue and the lesion segmentation. The idea of repeating the second and the third step is that the lesions are primarily WM, therefore, the T1 lesion filling will result in better brain tissues segmentation, which in turn results in better segmentation of lesions.

Optionally, after the last iteration, lesions are recovered from the GM in case the outlier belief is high. These lesions are added to the previously found lesions and then these final segmented lesions from the FLAIR 10 are dilated to better approach the volume of the lesions. Subsequently the T1 weighted image 20 is filled one more time and segmented, providing again the final segmentations of WM, GM and CSF.

Optionally, the volumes and count of the lesions is determined within different anatomical regions 600, for example by transforming the region labels from an anatomical atlas. This leads to final estimated values of WM, GM, and CSF volume 710, and a lesion count and volume 720.

The present invention also pertains to a system comprising an image processor configured to carry out the methods described above. The image processor may be implemented in dedicated hardware (e.g., ASIC), configurable hardware (e.g., FPGA), programmable components (e.g., a DSP or general purpose processor with appropriate software), or any combination thereof. The same component(s) may also include other functions.

Figure 4:
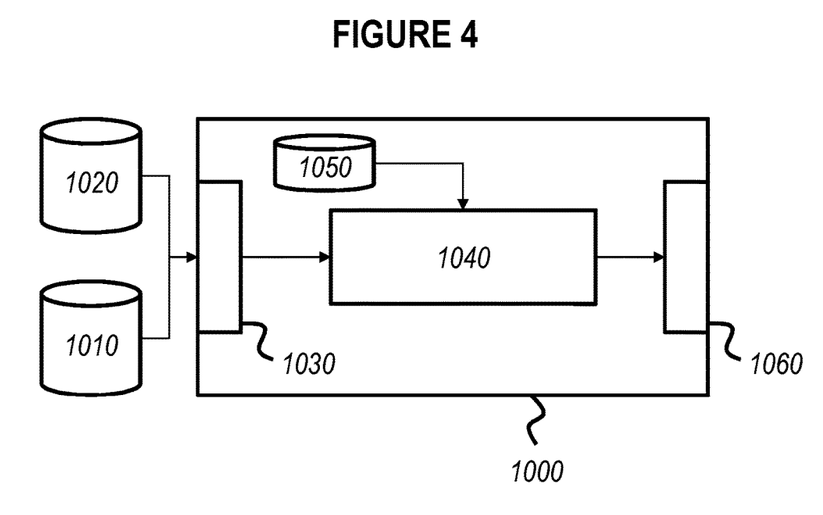
FIG. 4 schematically illustrates a system according to an embodiment of the present invention.

An exemplary design of such a system is schematically illustrated in FIG. 4. The system 1000 comprises an input interface 1030 adapted to receive the input images to be used from an image acquisition apparatus or a storage element. Without loss of generality, two storage elements 1010, 1020 are illustrated, representing respective storage devices for the FLAIR image 10 and the T1 image 20. The system 1000 further comprises a processor 1040, operatively connected to the input interface 1030 and an output interface 1060. The processor 1040 is capable of running a program stored in memory 1050, which is configured to cause the processor 1040 to carry out the method according to the present invention.

The term "interface" is used to designate the combination of hardware and software or firmware required to allow an exchange of data between the processor 1040 and the components providing or receiving the corresponding data. The input interface 1030 and the output interface 1060 may share common hardware. In particular, the interface may be a local area network (LAN) interface, such as an interface according to the IEEE 802.3 "Ethernet" standard, on which appropriate network and transport protocols are implemented, such as a TCP/IP stack. The interfaces may provide access to a storage area network (SAN) or network attached storage (NAS), which is intended to store the input images to be used and/or the result of the analysis. The interfaces may provide access to a wide area network (WAN) such as the Internet, which includes other computers that provide the input images to be used and/or retrieve the result of the analysis.

The present invention also pertains to a computer program product comprising code means configured to cause a processor configured to carry out the methods described above. The computer program product may comprise a computer readable medium, such as a magnetic tape, a magnetic disc, an optical disc, a semiconductor memory, or the like, having the code means stored thereon.

While the invention has been described hereinabove with reference to specific embodiments, this was done to clarify and not to limit the invention. The skilled person will appreciate that various modifications and different combinations of disclosed features are possible without departing from the scope of the invention.

The invention claimed is:

1. A method of analyzing image data, the method comprising:
   obtaining a first image of a first part of an object;
   obtaining a second image of a second part of the object, said second part having substantial overlap with said first part;
   obtaining a mapping between said first image and said second image;
   segmenting said second image to obtain a segmentation;
   detecting outliers in said first image by identifying extreme intensity values of elements within one or more classes of elements on the basis of said segmentation;
   replacing elements of said second image that correspond, according to said mapping, to at least some of said detected outliers of said first image, with replacement values, so as to obtain a corrected second image; and
   updating said segmentation by performing said segmenting on said corrected second image;
   wherein said detecting outliers, said replacing, and said updating are performed iteratively until a predetermined convergence criterion is met, said predetermined convergence criterion representing a point at which there is no significant change in the tissue and the lesion segmentation.

2. The method according to claim 1, wherein said outliers are detected by segmenting said first image starting from said segmentation of said second image with an additional outlier class.

3. The method according to claim 1, further comprising initiating said segmenting by transferring a segmentation of an example to said second image.

4. The method according to claim 1, wherein said obtaining of said mapping comprises performing a registration of said obtained first image to said obtained second image.

5. The method according to claim 1,
   wherein said object comprises at least a part of a brain, said first image is a FLAIR image, said second image is a T1 image;
   wherein said segmentation comprises a classification of elements of said T1 image as gray matter, white matter, or cerebro-spinal fluid; and
   wherein said outliers are detected among elements of said first image that are classified as white matter.

6. The method according to claim 5, wherein said replacement values are based on average values of elements classified as white matter in non-outlier elements in proximity of said respective outliers.

7. The method according to claim 5, further comprising removing elements representing non-brain tissue from said second image.

8. The method according to claim 5, wherein said segmentation is used to calculate respective volumes or areas of gray matter, white matter, and cerebro-spinal fluid.

9. The method according to claim 5, wherein said outlier detection is used to calculate volumes or areas of said outliers.

10. The method according to claim 8, further comprising the calculation of volumes or areas in different anatomical regions.

11. A non-transitory computer-readable medium having stored thereon executable instructions that when executed by one or more processors of an image processing system, cause the image processing system to performing the following:
    obtain a first image of a first part of an object;
    obtain a second image of a second part of the object, said second part having substantial overlap with said first part;
    obtain a mapping between said first image and said second image;
    segment said second image to obtain a segmentation;
    detect outliers in said first image by identifying extreme intensity values of elements within one or more classes of elements on the basis of said segmentation;
    replace elements of said second image that correspond, according to said mapping, to at least some of said detected outliers of said first image, with replacement values, so as to obtain a corrected second image; and
update said segmentation by performing said segmenting on said corrected second image;
wherein said detecting outliers, said replacing, and said updating are performed iteratively until a predetermined convergence criterion is met, said predetermined convergence criterion representing a point at which there is no significant change in the tissue and the lesion segmentation.

12. An image processing system comprising:

an input interface adapted to receive a first image of a first part of an object and a second image of a second part of said object, said second part having substantial overlap with said first part ;

a processor, operatively connected to said input interface; and an output interface, operatively connected to said processor and adapted to output results produced by said processor; and a memory, operatively connected to said processor, the memory having stored thereon executable instructions that when executed by the processor of the image processing system, cause the image processing system to performing the following:

obtain the first image of a first part of an object;

obtain the second image of a second part of the object, said second part having substantial overlap with said first part;

obtain a mapping between said first image and said second image;

segment said second image to obtain a segmentation;

detect outliers in said first image by identifying extreme intensity values of elements within one or more classes of elements on the basis of said segmentation;

replace elements of said second image that correspond, according to said mapping, to at least some of said detected outliers of said first image, with replacement values, so as to obtain a corrected second image; and update said segmentation by performing said segmenting on said corrected second image;

wherein said detecting outliers, said replacing, and said updating are performed iteratively until a predetermined convergence criterion is met, said predetermined convergence criterion representing a point at which there is no significant change in the tissue and the lesion segmentation.

* * * * *